United States Patent [19]

Peterson

[11] 4,168,382
[45] Sep. 18, 1979

[54] ω-ARYL-INTER-PHENYLENE-9-DEOXY PGD₁ COMPOUNDS

[75] Inventor: David C. Peterson, Portage, Mich.

[73] Assignee: The Upjohn Company, Kalamazoo, Mich.

[21] Appl. No.: 903,626

[22] Filed: May 8, 1978

Related U.S. Application Data

[62] Division of Ser. No. 809,249, Jun. 23, 1977, Pat. No. 4,142,052, which is a division of Ser. No. 614,244, Sep. 17, 1975.

[51] Int. Cl.² ............................................. C07C 177/00
[52] U.S. Cl. ...................................... 560/53; 562/463
[58] Field of Search ........................... 560/53; 562/463

[56] References Cited
PUBLICATIONS

Derwent Abstract, 690955-B, BE766009-Q, 10-20-71.
Derwent Abstract, 48794Y/28, BE850-204, 07-07-77.
Chem. Abstr., 86:43269n, Kunstmann, R., 02-09-76.
Chem. Abstr., 86:120868m, Skuballe, 28-10-76.

Primary Examiner—Paul J. Killos
Attorney, Agent, or Firm—Robert A. Armitage

[57] ABSTRACT

Prostaglandin analogs with the following cyclopentane ring structure:

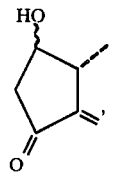

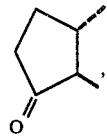

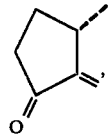

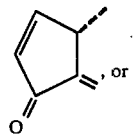

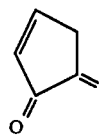

are disclosed along with intermediates useful in their preparation and processes for their preparation. These analogs are useful for some of the same pharmacological purposes as the prostaglandins, particularly and especially as blood platelet aggregation inhibitors.

25 Claims, No Drawings

ω-ARYL-INTER-PHENYLENE-9-DEOXY PGD₁ COMPOUNDS

The present invention is a divisional application of Ser. No. 809,249, filed June 23, 1977, now U.S. Pat. No. 4,142,052 issued Feb. 27, 1979; which is a divisional application of Ser. No. 614,244, filed Sept. 17, 1975, now pending. Likewise, U.S. Pat. No. 809,248, filed June 23, 1977, now U.S. Pat. No. 4,099,014 issued on July 4, 1978, is a divisional application of Ser. No. 614,244.

The present invention relates to prostaglandin analogs for which the essential material constituting a disclosure therefor is incorporated by reference here from U.S. Pat. No. 4,099,014.

I claim:

1. A prostaglandin analog of the formula

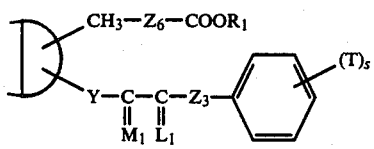

wherein D is

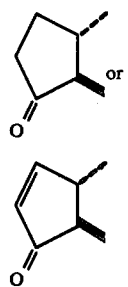

wherein Y is cis—CH=CH—, trans—CH=CH—, or —CH₂CH₂—;
wherein Z₆ is

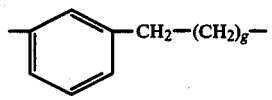 (1)

or

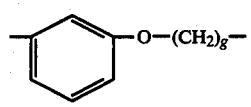 (2)

wherein g is one, 2, or 3;
wherein M₁ is

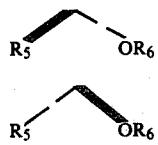

wherein R₅ and R₆ are hydrogen or methyl, with the proviso that one of R₅ and R₆ is methyl only when the other is hydrogen;

wherein L₁ is

or a mixture of

and

wherein R₃ and R₄ are hydrogen, methyl, or fluoro, being the same or different, with the proviso that one of R₃ and R₄ is hydrogen or fluoro only when the outer is hydrogen or fluoro;

wherein Z₃ is oxa or methylene;

wherein T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that more than two T's are other than alkyl, with the further proviso that Z₃ is oxa only when R₃ and R₄ are hydrogen or methyl, being the same or different; and wherein R₁ is hydrogen, alkyl of one to 12 carbon atoms, inclusive, cycloalkyl of 3 to 10 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation;

with the further proviso that D is

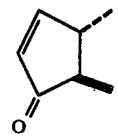

only when Y is —CH₂CH₂—.

2. A compound according to claim 1, wherein M₁ is

3. A compound according to claim 1, wherein M₁ is

4. A compound according to claim 3, wherein D is

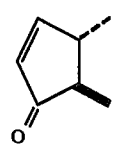

and Y is —CH₂CH₂—.

5. A compound according to claim 4, wherein Z₃ is methylene.

6. A compound according to claim 5, wherein s is zero or one and T is chloro, fluoro, or trifluoromethyl.

7. A compound according to claim 6, wherein g is one.

8. A compound according to claim 7, wherein $R_5$ and $R_6$ are both hydrogen.

9. A compound according to claim 8, wherein $R_3$ and $R_4$ are both hydrogen.

10. 3,7-Inter-m-phenylene-17-phenyl-4,5,6,18,19,20-hexanor-13,14-dihydro-9,10-didehydro-9-deoxy-PGD$_1$, a compound according to claim 9.

11. A compound according to claim 4, wherein $Z_3$ is oxa.

12. A compound according to claim 11, wherein s is zero or one and T is chloro, fluoro, or trifluoromethyl.

13. A compound according to claim 3, wherein D is

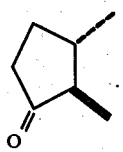

14. A compound according to claim 13, wherein $Z_3$ is methylene.

15. A compound according to claim 14, wherein s is zero or one and T is chloro, fluoro, or trifluoromethyl.

16. A compound according to claim 15, wherein g is one.

17. A compound according to claim 16, wherein $R_5$ and $R_6$ are both hydrogen.

18. A compound according to claim 17, wherein $R_3$ and $R_4$ are both nydrogen.

19. 3,7-Inter-m-phenylene-17-phenyl-4,5,6,18,19,20-hexanor-9-deoxy-PGD$_1$, a compound according to claim 18.

20. A compound according to claim 13, wherein $Z_3$ is oxa.

21. A compound according to claim 20, wherein s is zero or one and T is chloro, fluoro, or trifluoromethyl.

22. A compound according to claim 21, wherein g is one.

23. A compound according to claim 22, wherein $R_5$ and $R_6$ are both hydrogen.

24. A compound according to claim 23, wherein $R_3$ and $R_4$ are both hydrogen.

25. 3,7-Inter-m-phenylene-16-phenoxy-4,5,6,17,18,19,20-heptanor-9-deoxy-PGD$_1$, a compound according to claim 24.

* * * * *